United States Patent [19]

Welker

[11] Patent Number: 5,098,847

[45] Date of Patent: Mar. 24, 1992

[54] METHOD AND APPARATUS FOR PORTABLE TESTING OF PRODUCTS FROM PROCESSING COLUMN

[76] Inventor: Brian H. Welker, 13818 Florence Rd., Sugar Land, Tex. 77478

[21] Appl. No.: 571,701

[22] Filed: Aug. 24, 1990

[51] Int. Cl.⁵ .................................................. G01N 31/22
[52] U.S. Cl. .................................. 436/180; 73/864.62; 73/863.86
[58] Field of Search ...................... 436/180; 73/864.62, 73/864.51, 864.63, 864.91, 864.34, 864.35, 863.81–863.86, 863.71, 863.72, 863.73

[56] References Cited

U.S. PATENT DOCUMENTS

| | | | |
|---|---|---|---|
| 3,011,349 | 12/1961 | Kratz | 73/863.86 |
| 3,438,263 | 4/1969 | Cohen et al. | 73/863.86 |
| 3,795,347 | 3/1974 | Singer | 73/864.35 |
| 3,858,450 | 1/1975 | Jones | 73/863.72 |
| 3,910,764 | 10/1975 | Tower | 73/864.63 X |
| 4,063,460 | 12/1977 | Svensson | 436/180 X |
| 4,470,431 | 9/1984 | Shackelford et al. | 73/864.34 X |
| 4,580,453 | 4/1986 | Taylor | 73/863.86 |
| 4,599,315 | 7/1986 | Terasaki et al. | 436/180 X |
| 4,823,622 | 4/1989 | Nohl et al. | 73/863.71 |
| 4,925,627 | 5/1990 | Johnson | 73/863.81 X |

FOREIGN PATENT DOCUMENTS

| | | | |
|---|---|---|---|
| 2631797 | 1/1978 | Fed. Rep. of Germany | 73/864.62 |
| 2819554 | 11/1979 | Fed. Rep. of Germany | 73/864.62 |
| 1616 | 2/1989 | PCT Int'l Appl. | 73/864.62 |
| 836557 | 6/1981 | U.S.S.R. | 73/864.62 |
| 2125771 | 3/1984 | United Kingdom | 73/863.86 |

Primary Examiner—Tom Noland

[57] ABSTRACT

A portable test apparatus is set forth herein. It incorporates a twenty-two inch structure terminating in a protective cover with a loop for tool belt engagement by personnel climbing on chemical product processing equipment. The protective cover is removed by a quarter turn twist-lock mechanism. The test equipment includes a cylinder, a piston therein, heads at the opposite ends of the cylinder and valves to admit a sample measured thereto and further admitting product into the chamber and then from the chamber to test equipment through suitable control valve mechanisms.

10 Claims, 1 Drawing Sheet

U.S. Patent
Mar. 24, 1992
5,098,847
FIG. 1
FIG. 2
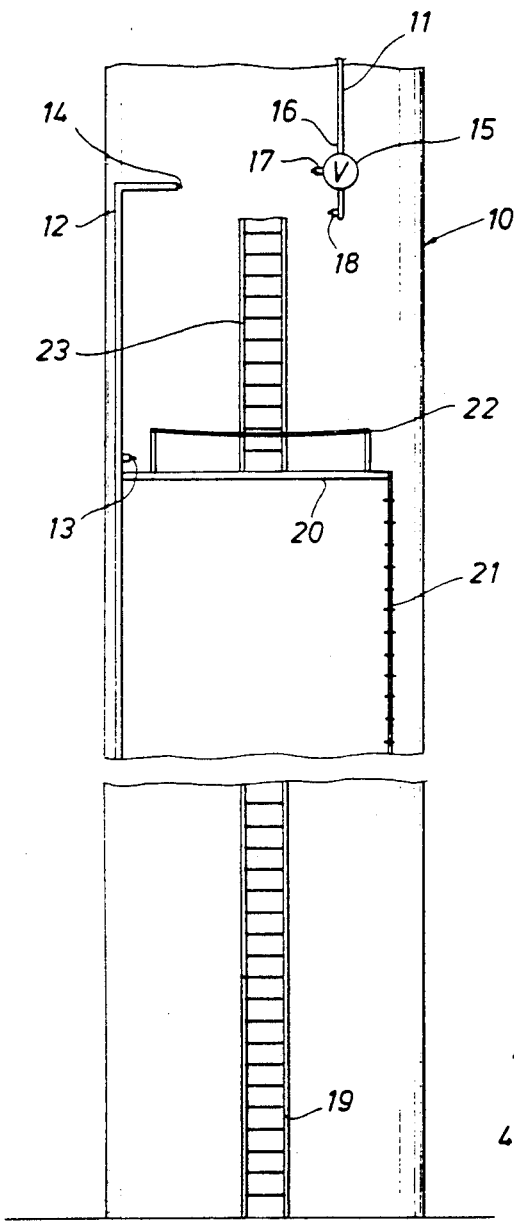
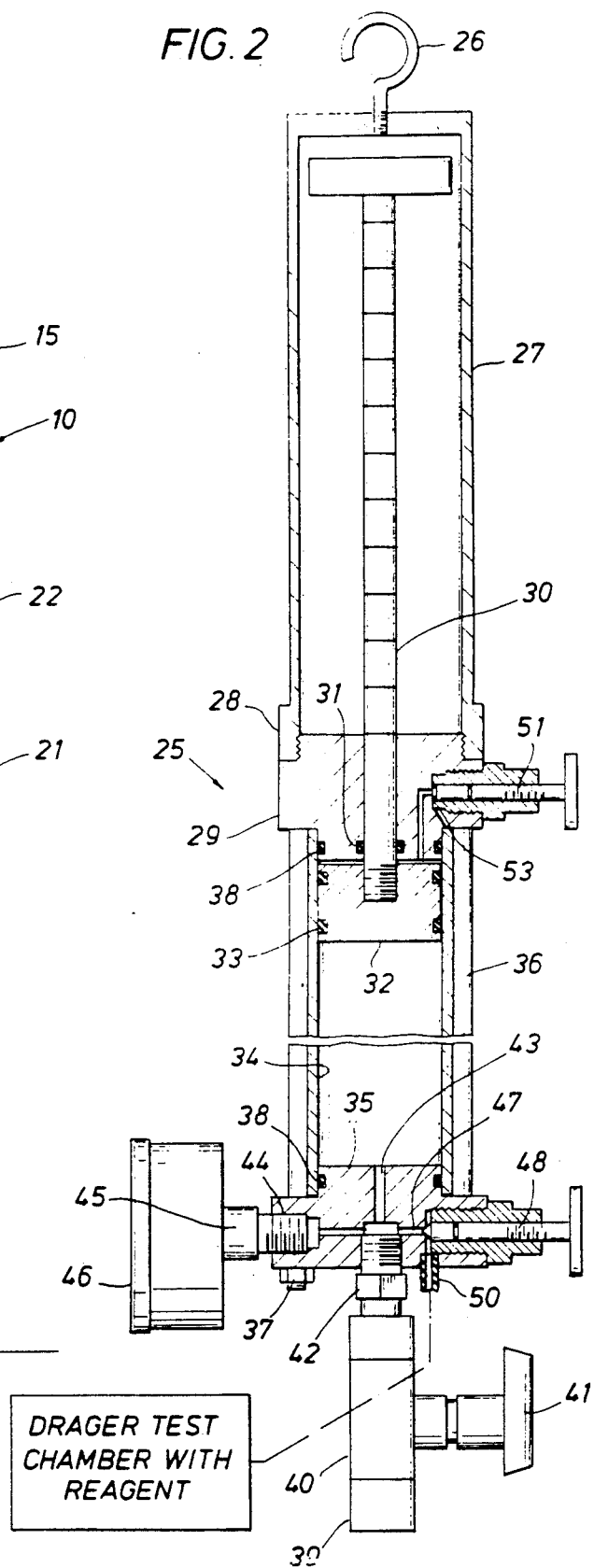
DRAGER TEST CHAMBER WITH REAGENT

METHOD AND APPARATUS FOR PORTABLE TESTING OF PRODUCTS FROM PROCESSING COLUMN

BACKGROUND OF THE DISCLOSURE

It is necessary to test products flowing through pipes, tubing, conduits, valves and the like of large processing plants. It is not uncommon to have a processing column which stands 200 feet tall and which is equipped with a number of pipes or conduits running along the column. At various locations, there may be valves, fittings and the like connecting with the process column. Some of these may be several inches in diameter for fluids at elevated pressures and temperatures. Other apparatus may connect through valves with packing glands and the like. It is necessary to periodically test for leaks or to test for unwanted constituents at various points on the column. A typical column operates at elevated pressure and temperature. The wall of the column is quite thick, sometimes ranging several inches in thickness to contain the high pressure process. Once installed, it is nearly impossible to make a hot tap into a column through a thick wall into an extremely high pressure merely for taking periodic samples. Accordingly, samples are obtained at limited locations such as on the feedlines running up and down such a column, or perhaps at valves and other fittings. Even still, it is necessary to make a severe reduction in diameter of the tap so that the small sample for testing purposes can be obtained. Regrettably, this may occur near the top of the column.

Such columns are equipped with platforms at spaced locations along the column and ladders are anchored to the side of the column to permit a person to climb the column. In climbing the column, a typical service person will have to carry hand tools with them to carry out the tasks at hand. In all, this makes gathering samples from various tapped sample points along the column difficult. It makes it especially difficult where it is necessary to obtain samples to check often for pollutants and the like.

The present apparatus is directed to a portable test equipment. It is a test system which can be carried by the operator who must first climb up the column to some great height. Sometimes, the test can be carried out with safety on a platform at some elevation on the column. Sometimes, the test must be carried out while on the column ladder. At this juncture, the test person is normally standing on the ladder with both feet on the ladder, one arm looped through the vertical frame members of the ladder with a safety belt hooked to the ladder at some location. Suffice it to say, these are difficult working circumstances. The present apparatus is a portable system for use in that circumstance. It is intended for use by a person operating in such circumstances to carry out a test. For instance, the test might be looking for impurities which might be leaking or otherwise escaping from some fitting. In that circumstance, the risk is quite high because of the physical environment encountered by the test person, and the test may have to be performed repetitively. The present apparatus is a system which enables the gathering of a small sample so that testing can be carried out. The present equipment is sized so that it can be hung on the tool belt which a service person normally wears. Moreover, it is a test system which enables collection of a sample of a specified size. The sample is collected within a chamber defined within a cylinder having a moveable piston. The piston moves between opposite heads on the device, the heads closing the chamber. At one end of the equipment, there is a handle which connects with an indicator rod marked with graduations thereon which shows the size of the sample in the chamber. The push rod can be forced into the closed chamber to move the piston when the volume stored in the chamber is negligible. As the volume increases to the maximum amount, an indicator marked on the indicator rod provides a measure of the total contents therein. The system is constructed with two heads at the opposite ends of the cylinder. On the backside of the piston, there is a chamber defined by the piston which moves against the remote head. That head includes a valve which permits evacuation of that chamber as required. In addition, one head of the equipment has an inlet line through a control valve which permits filling of the chamber. A pressure gauge is attached to that head to measure chamber pressure. A needle valve is likewise included so that the chamber can be discharged controllably to a test device. The present apparatus is preferably used with a Drager test unit which directs the discharge from the safety test equipment into a small container where it is exposed to reagents which forms selected colors wherein the colors indicate the nature of the material found on testing. The device of the present invention is thus connected through a first connection to the source of gas to be tested, and is also connected with the Drager test unit. These are the only two connections necessary for operation. The system includes a cap which telescopes over and locks in place to surround the extending indicator rod, and further is constructed with means for easily and conveniently hooking the apparatus on the belt. A built in pressure gauge is provided in one embodiment and filling occurs through a line connected to a product inlet valve. The device is relatively easy to use being provided with product inlet valve as mentioned, a Drager test valve, and an auxiliary valve for easy evacuation of the chamber. In summary, the device is a portable mechanism which enables a test to be carried out at difficult to achieve locations.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is a view showing an upstanding process tower of substantial height on which testing is to be carried out on a ladder or platform high above the ground; and FIG. 2 is a sectional view through a test apparatus which enables a test sample to be collected and delivered in controlled measure to a Drager test device.

BRIEF DESCRIPTION OF THE PREFERRED EMBODIMENT

Attention is now directed to FIG. 1 of the drawings where the numeral 10 identifies a processing column of substantial diameter and height. It is not uncommon to fabricate such columns with a diameter of sixteen feet and a height of 150-200 feet. They are typically constructed of substantially thick steel to enclose a process which operates at elevated pressures and temperatures, indeed pressures as high as 3,000 psi and temperatures in excess of 1,000° F. There may or may not be a furnace at the bottom. Typically the distillation column 10 is constructed with a number of lines on the exterior. Representative lines are included in the present instance, one being the line 11 which extends along the exterior and another being the line 12 which provides a feed which in input to the column. The line 12 is provided with a small tap 13 for connection through a suitable valve (omitted for sake of clarity) where fluid discharge can be obtained for test purposes. The line 12 includes another tap at 14 where the line 12 inserts into the process column to introduce or remove fluid under pressure. The line 11 connects with a valve 15. There are three taps at 16, 17 and 18. The three taps provide fluid above and below the valve, and perhaps fluid which might be leaking from the valve at the packing gland or elsewhere in the housing of the valve. In summary, the taps 13, 14, 16, 17 and 18 are included for providing test outlets. It will be appreciated that it is preferable to provide these taps rather than a tap into or through the column wall or shell making up the column.

The column incorporates a first ladder segment 19 which extends up the side of the column for personnel to climb. They may ultimately climb to a small platform 20 which is located at one or multiple locations along the column. An additional ladder segment 21 is incorporated along the column below the platform 20. The platform may have a safety rail 22. Another ladder segment 23 extends thereabove. This ladder segment passes near to or within arms length of the fittings 14, 16, 17 and 18 which are provided for personnel to engage, thereby testing the makeup or condition of the fluid at those locations.

Going now to FIG. 2 of the drawings, the number 25 identifies the test apparatus of the present disclosure which in the preferred embodiment measures only about twenty-two inches in length. It is provided with a hook or eyelet 26 which enables the device to be hung from the belt of the user. The eyelet 26 is centered at the top end of a protective cover 27 which terminates in an enlarged shoulder 28. The shoulder is equipped with notches and undercut grooves on the interior to serve as a J-slot lock mechanism. This is a quarter turn twist lock fastener which enables the protective cover to be anchored to a cylindrical head 29. The head 29 is axially hollow to support a moveable graduated indicator rod 30. The rod 30 moves through appropriate seals at 31 where it passes through the head. The rod 30 threads to or joins with a cylindrical piston 32. The piston 32 supports appropriate seal rings 33 on the exterior which seal the piston within a surrounding cylinder 34. The cylinder extends to a second head 35, the heads 29 and 35 being joined by a set of long tie bolts 36 which extend between the two heads and which are fastened with suitable nuts 37. The nuts are pulled tight so that the two heads are pulled together on the cylinder 34. Moreover, the nuts in conjunction with the tie bolts place pressure on the cylinder so that the two heads are pulled snugly against the cylinder defining a fixed measurable volume therein which is calibrated to match the operation of the graduated indicator rod 30. The rod 30 is marked at regular distances with marks indicative of a specified size, and a suitable measure is twenty cubic centimeter increments so that the maximum capacity is 200 cc in the chamber. Both the heads are provide with suitable O-rings at 38 for sealing purposes.

Both of the heads on the cylinder support valves and passages as will be described. There is a product inlet fitting 39 which connects with a hand operated ball or plug valve 40 provided with a handle 41. It is opened or closed to permit flow into the fitting 42 which in turn opens into a passage 43 to fill the chamber in the cylinder 34. The passage 43 communicates through a side passage to a tapped opening 44 which receives a threaded fitting 45 which connects with a gauge 46. In addition to this, there is a passage 47 which connects with a needle valve 48 which opens or closes to provide controlled fluid flow through a Drager test port 50 which extends to a Drager test instrument. A Drager test instrument is a mechanism which provides a chemical reagent in a mixing container so that introduction of a fluid through the port 50 reacts with the test reagent, thereby forming an indication of specified test materials. In ordinary use, the test routine is carried out with the Drager test unit so that constituents in the fluid undergoing tests may be detected. This will become more clear on a description of a test procedure.

The test equipment 25 is hung on the belt of personnel who then climb up the tower with the present equipment. The equipment illustrated in FIG. 2 of the drawings is the key apparatus required along with the Drager test kit, a hose for connection from the port 50 to the Drager test kit, and a second hose connecting to the product inlet 39. The two hoses are normally rather short and are typically provided with universal type fittings for easy connection and disconnection. With this equipment, the personnel will then climb the tower to the appropriate height. Typically using a safety belt for security, the person will ultimately climb the ladder 23, fasten the safety belt at a particular location on the ladder and make appropriate connections to one of the fittings 14, 16, 17 or 18 for test purposes.

The connection sequence occurs in the following manner. First of all, a hose is connected to the fitting 18, for example, and is then extended to the fitting 39. A quantity of the product is flowed through the hose to clear the hose of air and the latter connection is then made. The protective cover 27 is detached by a quarter rotation turn, enabling the cover to hang from the tool belt. With one hand, the apparatus is held around the cylinder 34 and the valve 40 is opened. Ordinarily, the piston 32 is closed by positioning it to the far right; it is then forced to the left. Movement to the left would ordinarily build up an opposing pressure which must be vented. To this end, the apparatus includes a needle valve 51 which provides a bleed path utilizing the passage 52 which extends to the valve, and a vent passage 53 to atmosphere, this valve is opened to enable venting. As the piston is moved to the left, the chamber on the right is filled with the fluid product delivered from the process. After the chamber has been filled, the valve 40 can then be conveniently closed. Next, the Drager test unit is connected by a tubing at the port 50. Typically, this is accomplished while cradling the Drager test unit and the test apparatus 25 on the safety belt against the ladder whereupon both hands are free to make the connection and thereafter carry out the test. The test is conducted merely by opening the valve 48. When the valve is opened, this clears the passageway for fluid flow from the chamber into the Drager test unit. By hand, the indicator rod 30 is forced to the right, moving the piston in the chamber to force the fluid from the chamber so that the fluid flow is delivered for testing. The piston is used to force fluid into the test unit. The test unit normally tests for such specific compounds as $H_2S$. mercaptans, chlorides or ammonia compounds. This test varies dependent on the reagent. Moreover, this is variable dependent on the particular reagent used in the process. It is sufficient to note that several types of different test reagents can be used for detection of all sorts of compounds or radicals.

One other feature of the present apparatus worth noting is the fact that disconnection is achieved easily. There are two hoses which are connected, as mentioned above, and they are quickly disconnected and can be stored by the personnel typically on the tool belt, the Drager test unit can then be placed in a storage pouch, and the test apparatus 25 can be stored by reconnecting it with the protective cover so that it hangs from the tool belt. The test procedure can be visually observed during operation. The gauge 46 can be observed so that the Drager test can be monitored visually both for test results and pressures achieved during the test. Moreover, observation of the gauge provides assurance that a product has been safely received from the process. For instance, if the valve 40 is opened while the valve 48 is closed, the pressure observed by the gauge 46 should approach that which prevails in the supply line. This is normally a known or stable pressure. The present apparatus will reflect that pressure to give assurances that the fluid process undergoing testing has been properly tapped.

The present apparatus can be moved from fitting to fitting on the column. This may require the operator to climb up or down the ladders on the column. Various different connective points can be located and tested in a portable fashion. The present apparatus is particularly useful for carrying out such procedures. For calibration purposes, the cylinder 34 is sized to a particular size such as 200 cc so that the full charge of 200 cc is delivered to the Drager test unit. The equipment is therefore relatively small, having a length of about twenty-two inches constructed as illustrated for this size, and also is relatively light, weighing less than ten pounds even when equipped with the gauge 46. The gauge can be omitted for convenience sake if pressure measurements are not important. However, it is preferable to use the gauge to assure that the chamber is connected with the high pressure source. The indicator rod serves as a filling indicator. The ordinary procedure involves initially pushing the piston 32 to the far right so that the chamber is reduced to zero volume. As mentioned, the hose is preferably purged of air prior to use. In similar fashion, when the product undergoing test is delivered, the piston is forced to the left, extending the indicator rod visibly and providing an increased pressure when the chamber has been filled. The valves are operated in the required sequence so that the test is then ready to be run. By use of the present apparatus, testing can be carried out on a routine procedure. For instance, if it is suspected that the valve 15 is leaking, the test personnel can use this equipment by connection at the fitting 17 on the valve to determine leakage from the housing of the valve. This equipment can also be used to test for other materials in the vicinity of the equipment.

While the foregoing is directed to the preferred embodiment, the scope thereof is determined by the claims which follow.

What is claimed is:

1. A method of conducting a test at a remote, inconvenient, dangerous or unaccessible location on a chemical processing plant which comprises the steps of:
   (a) in a test chamber defined by a cylinder between two heads including a piston therein, the preliminary step of closing the test chamber to minimum volume by moving the piston to one end of the chamber;
   (b) moving a portable test equipment to the location on the chemical processing plant where the test is to be performed, the portable test equipment containing said test chamber;
   (c) connecting a product supply line from the chemical processing plant to the test equipment to obtain a fluid sample therefrom for delivery into the test chamber of the portable equipment;
   (d) filling the chamber in the test equipment to a specified amount with a measured volume of the product from the chemical process plant wherein this step is accompanied by forming an indication visible to the personnel that the chamber has been filled, wherein the filling step fills sufficiently with the product to force the piston toward an opposite end of the chamber and including the step of evacuating the chamber at the opposite end to enable piston movement, and further including the step of operating a valve means to isolate the chamber after filling;
   (e) testing the product in the chamber with a reagent wherein the testing is accomplished by forcing the product from the chamber into a test system having a reagent therein, and further wherein an indication of the test results is obtained; and
   (f) disconnecting the product supply line from the processing plant.

2. The method of claim 1 including the step of hand supporting the test apparatus while standing on the processing plant, and further testing for selected products from the processing plant during personnel attendance.

3. The method of claim 2 wherein a personnel climbs on the processing plant to locate a fitting thereof furnishing the fluid sample, and then connecting the product supply line to the fitting to enable immediate testing.

4. The method of claim 3 wherein the personnel carries the portable test equipment suspended from his person and connects the test equipment to the fitting for operation while attending to the test equipment.

5. The method of claim 4 including the step of connecting the test system to the portable test equipment via a flow line, and observing the visible indication by the personnel climbing on the processing plant.

6. The method of claim 1 including the initial step of supporting the portable test equipment releasably hooked onto a personnel within a quickly disconnected container means therefor, and wherein the personnel then climbs to a selected location on the processing plant using ladders and platforms thereon, and including the further steps of releasably connecting the supply line to a fitting on the processing plant to obtain the product flow and also connecting the supply line to the portable test equipment after positioning the portable test equipment accessible for personnel hand operation near the fitting; and when testing is completed, disconnecting the supply line, and positioning the portable test equipment for personnel climbing on the processing plant to leave the processing plant.

7. The method of claim 6 including a pretest step of removing the test equipment from said container means, then making the supply line connection thereto, and restoring the test equipment to said container means for post test climbing on the processing plant.

8. The method of claim 7 wherein the step of removing the test equipment form said container means includes the step of relatively rotating the test equipment to said container means, and pulling the test equipment from said container means.

9. The method of claim 8 including the post test step of storing the test equipment in said container means and relatively rotating to a locked and stored condition.

10. A method of conducting a test at a remote, inconvenient, dangerous or unaccessible location on a chemical processing plant which comprises the steps of:
  (a) hand moving a portable test equipment to a remote or otherwise unaccessible location on the chemical processing plant where the test is to be performed and then including the step of hand supporting the test apparatus while standing on the process plant;
  (b) at the remote or otherwise unaccessible location, connecting a product supply line from the chemical processing plant to the test equipment to obtain a fluid sample therefrom for delivery into a chamber thereof wherein the chamber is defined by a cylinder between two heads including the piston therein and further including the preliminary step of closing the chamber to minimum volume by moving the piston to one end of the chamber, and filling sufficiently with the product to force the piston toward an opposite end of the chamber and including the step of evacuating the chamber at the opposite end to enable piston movement;
  (c) filling a chamber in the test equipment of specified size with a measured volume of the product from the chemical process plant wherein this step is accompanied by forming an indication visible to personnel that the chamber has been filled and further including the step of operating a valve means to isolate the chamber after filling;
  (d) testing the product in the chamber with a reagent wherein the testing is accomplished by forcing the product from the chamber into a test system and mixing the reagent with the product and further wherein an indication of the test results is obtained; and
  (e) disconnecting the product supply line from the processing plant to permit removal of the test equipment.

* * * * *